United States Patent
Carls et al.

(10) Patent No.: US 8,685,026 B2
(45) Date of Patent: Apr. 1, 2014

(54) DEVICES AND METHODS FOR RELEASING TENSION ON A SURGICAL TETHER

(75) Inventors: Thomas A Carls, Memphis, TN (US); Randall Noel Allard, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1488 days.

(21) Appl. No.: 12/126,116

(22) Filed: May 23, 2008

(65) Prior Publication Data

US 2009/0292286 A1 Nov. 26, 2009

(51) Int. Cl.
*A61B 17/56* (2006.01)

(52) U.S. Cl.
USPC .......................................................... 606/74

(58) Field of Classification Search
USPC .................. 606/74, 232, 233, 151–157, 246, 606/250–252, 254–255, 257, 258, 263
See application file for complete search history.

(56) References Cited

U.S. PATENT DOCUMENTS

| | | | |
|---|---|---|---|
| 4,854,304 A | 8/1989 | Zielke | |
| 6,287,308 B1 | 9/2001 | Betz et al. | |
| 6,296,643 B1 | 10/2001 | Hopf et al. | |
| 6,299,613 B1 | 10/2001 | Ogilvie et al. | |
| 6,402,751 B1 | 6/2002 | Hoeck et al. | |
| 6,436,099 B1 | 8/2002 | Drewry et al. | |
| 6,616,669 B2 | 9/2003 | Ogilvie et al. | |
| 6,623,484 B2 | 9/2003 | Betz et al. | |
| 6,746,450 B1 | 6/2004 | Wall et al. | |
| 6,761,719 B2 | 7/2004 | Justis et al. | |
| 6,783,527 B2 | 8/2004 | Drewry et al. | |
| 6,821,277 B2 | 11/2004 | Teitelbaum | |
| 6,899,713 B2 | 5/2005 | Shaolian et al. | |
| 6,960,213 B2 * | 11/2005 | Chervitz et al. | 606/74 |
| 7,018,379 B2 | 3/2006 | Drewry et al. | |
| 7,101,398 B2 * | 9/2006 | Dooris et al. | 606/151 |
| 2001/0029375 A1 | 10/2001 | Betz et al. | |
| 2003/0023241 A1 | 1/2003 | Drewry et al. | |
| 2003/0109874 A1 | 6/2003 | Dennis | |
| 2004/0087954 A1 * | 5/2004 | Allen et al. | 606/74 |
| 2005/0203514 A1 | 9/2005 | Jahng et al. | |
| 2006/0004367 A1 | 1/2006 | Alamin et al. | |
| 2006/0106381 A1 | 5/2006 | Ferree et al. | |
| 2006/0155279 A1 | 7/2006 | Ogilvie | |
| 2006/0190030 A1 | 8/2006 | To et al. | |

* cited by examiner

*Primary Examiner* — Heidi M Eide (57) ABSTRACT

The present application is directed to devices and methods for releasing tension on a surgical tether. In one embodiment, the release mechanism is constructed to be positioned between a locked position and a release position. In the locked position, the release mechanism is attached to the tether to prevent the tether from moving through the release mechanism. In the release position, the release mechanism allows the tether to move through the body. The release mechanism may be constructed to move between the release and locked positions after being implanted within a patient. In one embodiment, the release mechanism returns to the locked position after the tension on the tether has been reduced below a predetermined amount.

11 Claims, 5 Drawing Sheets

DEVICES AND METHODS FOR RELEASING TENSION ON A SURGICAL TETHER

BACKGROUND

The present application is directed to devices and methods for releasing tension on surgical tethers and, more particularly, to release mechanisms and methods that operate in vivo to release excessive tension on a tether.

The spine is divided into four regions comprising the cervical, thoracic, lumbar, and sacrococcygeal regions. Vertebral members of the spine are aligned in a curved configuration that includes a cervical curve, thoracic curve, and lumbosacral curve. Various deformities may affect the normal alignment and curvature of the vertebral members. Scoliosis is one example of a deformity of the spine in the coronal plane, in the form of an abnormal curvature. While a normal spine presents essentially a straight line in the coronal plane, a scoliotic spine can present various lateral curvatures in the coronal plane. The types of scoliotic deformities include thoracic, thoracolumbar, lumbar or can constitute a double curve in both the thoracic and lumbar regions. Schuermann's kyphosis is another example of a spinal deformity that affects the normal alignment of the vertebral members. One or more tethers may be attached to the vertebral members to reduce and/or eliminate the deformity.

Tethering is used with patients with growth potential of the bony members including prepubescent children less than ten years old who have yet to experience a growth spurt, and adolescents from 10-12 years old with continued growth potential. One issue with current tethering techniques is the inability to limit an amount of tension the tether applies to a vertebral member as the patient grows. This could lead to excessive stress on the bone interface. Current tethering techniques require a subsequent surgical procedure to lengthen the tether.

Tethering may also be used in other medical applications. One example is treatment of a fractured bone. In this context, the tether is attached to the bone on each side of the fracture. The tether is tensioned to apply a force that facilitates healing of the fracture. It may also be necessary to limit the amount of tension to ensure proper healing of the fracture.

SUMMARY

The present application is directed to devices and methods for releasing tension on a surgical tether. In one embodiment, the release mechanism is constructed to be positioned between a locked position and a release position. In the locked position, the release mechanism is attached to the tether to prevent the tether from moving through the release mechanism. In the release position, the release mechanism allows the tether to move through the body. The release mechanism may be constructed to move between the release and locked positions after being implanted within a patient. In one embodiment, the release mechanism returns to the locked position after the tension on the tether has been reduced below a predetermined amount.

The aspects of the various embodiments may be used alone or in any combination, as is desired.

DETAILED DESCRIPTION

Figure 1:
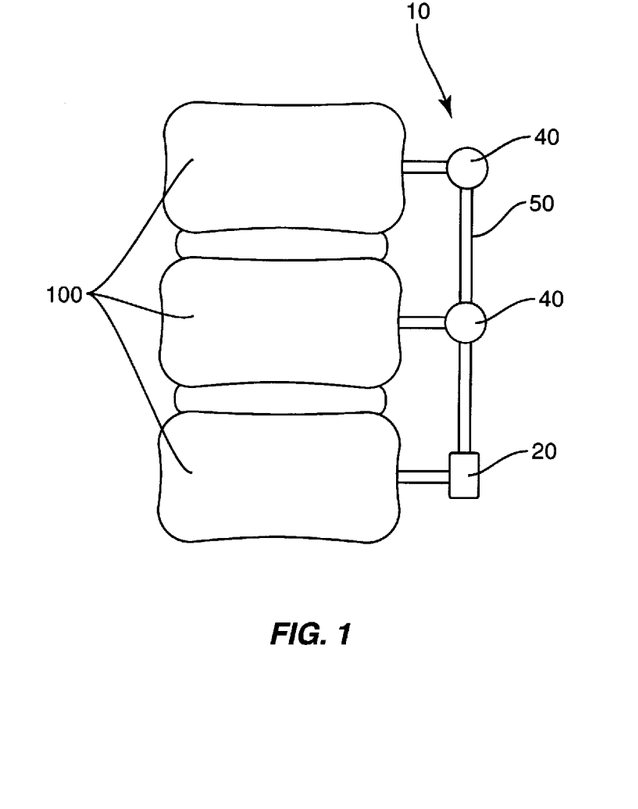
FIG. 1 is a schematic view of a tethering system according to one embodiment.

The present application is directed to devices and methods of releasing tension on a surgical tether. FIG. 1 schematically illustrates one embodiment of a tethering system 10 that includes a release mechanism 20 operatively connected to a tether 50. The tether 50 is attached to bony members 100 by one or more anchors 40 and applies a corrective force to the bony members 100. The release mechanism 20 releases the tension on the tether 50 in vivo if the force exceeds an amount that may cause damage. In one embodiment, the corrective force increases as a result of the patient growing after the tethering system 10 is initially inserted.

Figure 2:
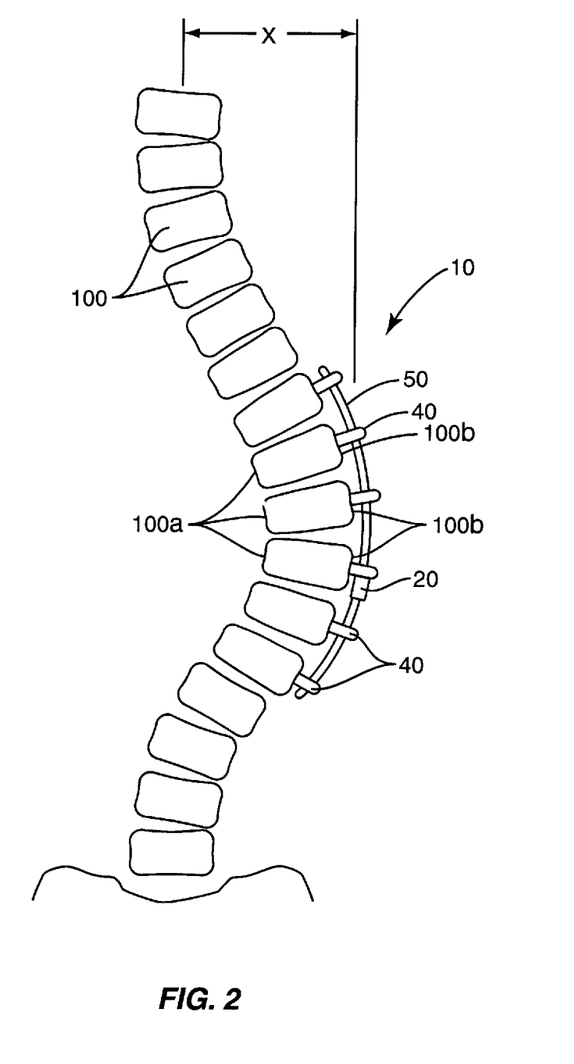
FIG. 2 is a schematic view of a tethering system attached to vertebral members according to one embodiment.

The tethering system 10 may be used for treating a variety of ailments within the patient. FIG. 2 illustrates one context for use in treating a scoliotic spine. This spine has a scoliotic curve with an apex of the curve being offset a distance X from its correct alignment in the coronal plane. In this embodiment, the bony members 100 are vertebral members that form the spine. The spine is deformed laterally so that the axes of the vertebral members 100 are displaced from the sagittal plane passing through a centerline of the patient. In the area of the lateral deformity, each of the vertebral members 100 includes a concave side 100a and a convex side 100b. In this embodiment, the tether 50 extends along the convex side 100b of two or more adjacent vertebral members 100. The tether 50 minimizes or arrests growth on the convex or "long" side of the spine and allows the concave or "short" side of the spine to grow and catch up with the long side. Alternatively, the tether 50 may treat the spinal deformity by simply preventing further misalignment such as curve progression.

Figure 3:
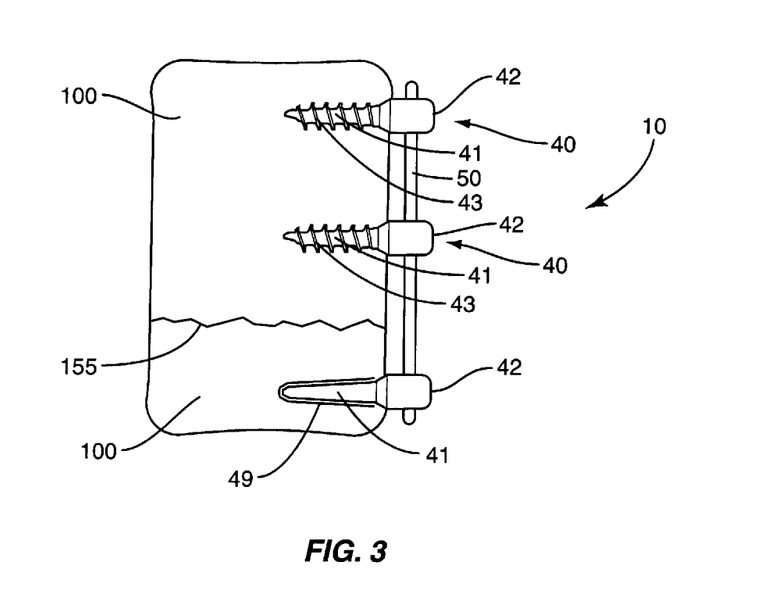
FIG. 3 is a schematic view of a tethering system attached to a fractured bony member according to one embodiment.

FIG. 3 illustrates another context of use with the tethering system 10 attached to a fractured bony member 100. The bony member 100 may be any of numerous members within the patient. One or more anchors 40 are positioned on each side of a fracture 155 to attach the tether 50 to the member 100 and apply tension that facilitates healing of the fracture 155.

Various anchors 40 may be used to attach the tether 50 to the bony members 100. FIG. 3 illustrates an embodiment with the anchors 40 including a shaft 41 that extends into the bony member 100. Shaft 41 may further include threads 43 to facilitate insertion and attachment with the bony member 100. An adhesive 49 may be placed on the shaft 41 to increase the attachment with the bony member 100. In one embodiment, the shaft 41 is coated with any number of osteoinductive or osteoconductive materials to enhance attachment as desired. Anchors 40 may also include a head 42 that extends outward from the shaft 41 and is constructed to receive the tether 50. In one embodiment, the head 42 includes a channel sized to receive the tether 50.

A variety of different tethers 50 may be used for treating the bony members 100. Embodiments include but are not limited to cables, artificial or synthetic strands, rods, plates, and springs. In one embodiment, tether 50 comprises an inner core with an outer sheath. The inner core and outer sheath may be made of a braided polymer such as polyester, polypropylene, or polyethylene. In one specific embodiment, the inner core and outer sheath are both made of polyethylene with the inner core being braided for strength and the outer sheath being braided for abrasion resistance. In one embodiment with the tether 50 being a strand, the strand may be manufactured from a variety of materials, including, but not limited to, conventional biocompatible implant alloys such as titanium, stainless steel, cobalt-chrome alloys, or even shape memory alloys and materials such as nickel-titanium.

The release mechanism 20 releases the tether 50 to reduce or remove the tension on the tether 50 and the force being applied to the one or more bony members 100. The release mechanism 20 is constructed to release the tension once the amount of tension exceeds a predetermined amount. Excessive tension may dislodge one or more of the anchors 40 from the bony members 100, or otherwise damage the bony members 100 or prevent proper alignment. The release mechanism 20 may completely release the tether 50 such that there is no tension remaining, or may release the tether 50 a limited amount such that a lesser amount of tension remains on the tether 50. The release of the tension may prevent a second surgical procedure that otherwise may be required. The release may also prevent damage to the bony members 100 that may be caused by the application of an excessive amount of tensile force. In one embodiment, an excess tensile force causes the anchors 40 to plow or otherwise extract from the bony members 100. Further, the release mechanism 20 functions after being implanted into the patient to prevent the necessity of a second surgery.

Figure 4:
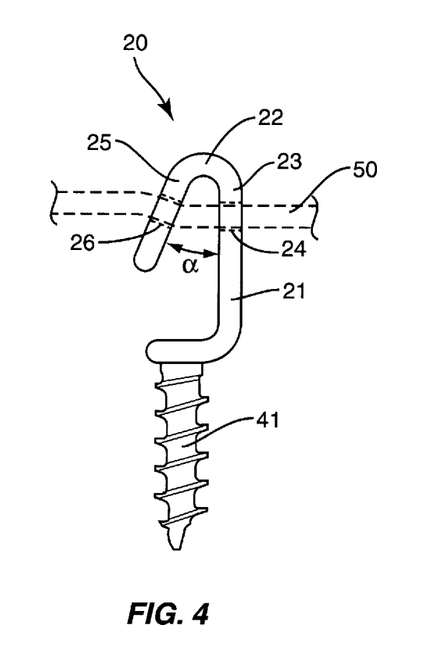
FIG. 4 is a side view of a release mechanism according to one embodiment.

FIG. 4 illustrates one embodiment of a spring clip release mechanism 20. The release mechanism 20 includes an elongated body 21 that includes first and second sections 23, 25 separated by a bend 22. Apertures 24, 26 are each positioned in one of the first and second sections 23, 25 and are each sized to receive the tether 50. The body 21 is constructed of a flexible material that causes the bend 22 to move and adjust the relative position and distances of the sections 23, 25. FIG. 4 illustrates the release mechanism 20 in a locked position that prevents the tether 50 from moving through the apertures 24, 26. The edges of the apertures 24, 26 are contact edges that engage with the tether 50. The sections 23, 25 are positioned to form an angle α when less than the predetermined amount of force is applied to the tether 50. At angle α, the tether 50 is captured within the apertures 24, 26 and is unable to move. Force applied to the tether 50 causes the bend 22 to flex and decrease the angle α. This flexing movement causes the apertures 23, 25 to align thus allowing the tether 50 to move and release the tension. In one embodiment, the sections 23, 25 are parallel in the release position. Once the tether 50 moves through the apertures 24, 26 and the tension is below the predetermined amount, the bend 22 flexes outward (i.e., the angle α increases) and the tether 50 is again captured.

In one embodiment, the bend 22 gradually flexes as the force is increased on the tether 50. Once the predetermined amount of force is applied to the tether 50, the bend 22 has moved enough such that the apertures 24, 26 are aligned and allow movement of the tether 50. In one embodiment, the bend 22 does not flex until the force exceeds the predetermined amount.

Figure 5:
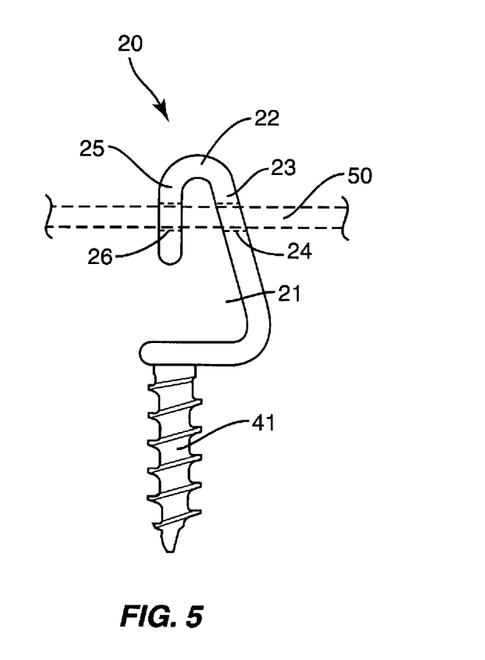
FIG. 5 is a side view of a release mechanism according to one embodiment.

The body 21 may include a variety of shapes and sizes. FIG. 4 includes one embodiment with the first section 23 being substantially parallel with a shaft 41, and the second section 25 being positioned at an oblique angle relative to the shaft. FIG. 5 includes an inverted embodiment with the first section 23 positioned at an oblique angle and the second section 25 being parallel to the shaft 41.

The body 20 may be constructed such that both sections 23, 25 move during flexing of the bend 22. In another embodiment, one of the sections 23, 25 is stationary with the movement being isolated to the other section. In the embodiments of FIGS. 4 and 5, the body 21 is constructed of a single elongated member. In other embodiments, the body 21 is constructed from two or more pieces connected together. In one specific embodiment, the bend 22 is a separate piece that is attached to each of the first and second sections 23, 25.

Figure 6:
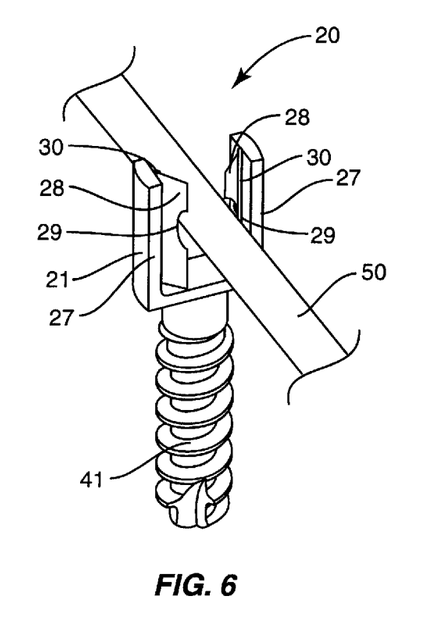
FIG. 6 is a perspective view of a release mechanism according to one embodiment.

FIG. 6 illustrates an embodiment of a gated release mechanism 20. The release mechanism includes a body 21 with a pair of spaced-apart arms 27 that form a channel sized to receive the tether 50. In one embodiment, the body 21 includes a U-shape with the arms 27 positioned on opposite sides of the channel. Gates 28 are pivotally connected to each of the arms 27 and each includes a contact edge 29 that is positionable within the channel. In one embodiment, one or both contact edges 29 include a cutout section. The cutout sections may include a variety of shapes, including but not limited to semi-circular, semi-rectangular, and semi-oval. A biasing member 30 is operatively connected to and biases each gate 28 towards a locked position.

When the gates 28 are in the locked position, a width of the opening formed between the contact edges 29 is less than the tether 50. This causes the tether 50 to be captured and unable to move through the release mechanism 20. When the tension on the tether 50 exceeds a predetermined amount, the gates 28 pivot thus causing the width of the opening between the contact edges 29 to increase and allow the tether 50 to move through the release mechanism 20. Once the force on the tether 50 is again below the predetermined amount, the gates 28 return to the locked position to again capture the tether 50.

Figure 7A:
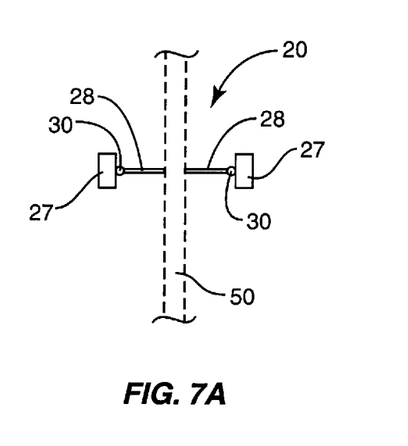
FIG. 7A is a top schematic view of the release mechanism of FIG. 5 in a locked position.
Figure 7B:
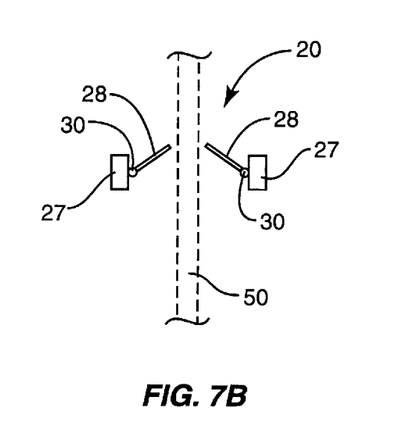
FIG. 7B is a top schematic view of the release mechanism of FIG. 5 in a release position.

FIG. 7A schematically illustrates the release mechanism 20 of FIG. 6 in the locked position, and FIG. 7B illustrates the release mechanism 20 in the release position. As illustrated in FIG. 7A, the gates 28 are aligned towards each other. In the locked position, the gates 28 may be parallel, or may be positioned at a non-parallel angle. The force of the biasing members 30 maintains the gates 28 in the locked position to prevent movement of the tether 50. In one embodiment, the arms 27 include a stop to limit the movement of the gates 28 in one direction. When the force on the tether 50 exceeds the predetermined amount, the force on the gates 28 applied through the tether 50 exceeds the force of the biasing members 30. This results in the gates moving to the release position as illustrated in FIG. 7B. This movement causes the distance between the contact edges 29 to increase and allows the tether 50 to move through the release mechanism 20. Once the force applied on the gates 28 through the tether 50 becomes less than the force of the biasing members 30, the gates 28 return to the locked position to again capture the tether 50.

The gates 28 may gradually move from the locked position as the force applied to the tether 50 increase. In another embodiment, the gates 28 do not move until the force exceeds the predetermined amount. A variety of biasing members 30 may be used to force the gates 28 towards the locked position. Examples include but are not limited to a spring and a flexible material such as stainless steel, titanium, memory metal, and memory polymer. The same or different types of biasing member 30 may be used on each gate 28.

Figure 8:
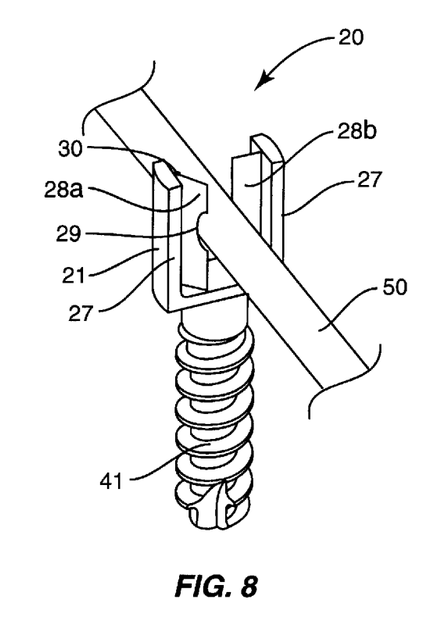
FIG. 8 is a perspective view of a release mechanism according to one embodiment.

FIG. 8 illustrates a similar embodiment with gate 28a being stationary and gate 28b being movable. Movable gate 28b is similar to the gates 28 explained for the embodiments of FIGS. 6 and 7A-7B. Gate 28a is fixedly positioned and extends from the arm 27 into the channel to contact against the tether 50. This release mechanism 20 operates in the same manner with the movable gate 28 moving between locked and released positions to adjust a width of the opening formed by the contact edges 29.

The contact edges 29 may include various sizes and shapes. The sizes and shapes may be the same or different on the gates 28. In one embodiment as illustrated in FIG. 8, a cutout section is positioned on just one gate 28a, with the opposing gate 28b including a substantially straight edge.

Figure 9:
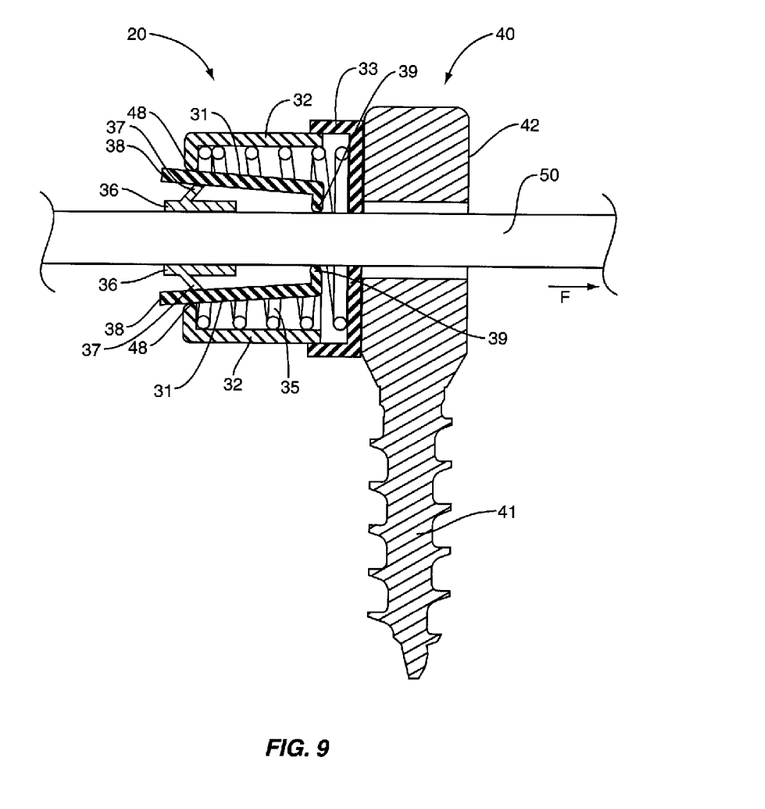
FIG. 9 is a sectional view of a release mechanism according to one embodiment.

FIG. 9 illustrates another release mechanism 20. This embodiment features a biasing member 35 positioned within a compressible frame that includes a first section 32 and a second section 33. Members 36 extend around a portion or entirety of the tether 50 and include extensions 37 that extend outward away from the tether 50. As illustrated in FIG. 9, the extensions 37 contact an inner surface of the spikes 31 that are pivotally attached to the members 36. The spikes 31 are constructed to pivot such that first ends 38 are positioned away from the tether 50 and contact edges 39 are in contact with the tether 50 when the release mechanism 20 is in the locked position. The spikes 31 and members 36 may each be constructed from one or more sections.

In the embodiment of FIG. 9, the release mechanism 20 is in a locked position with the second frame section 33 positioned against the anchor 40. The biasing member 35 biases the first frame section 32, the spikes 31, and the members 36 outward and away from the second frame section 33. Contact ends 48 of the first frame section 32 contact the spikes 31 at points inward from the extension 37 such that the spikes 31 pivot inward with the contact edges 39 engaging the tether 50.

In one embodiment, the spikes 31 include a frusto-conical shape with a distance between the spikes 31 increasing away from the first and second sections 33. In one embodiment, the extensions 37 are positioned outside of the first section 32 when the release mechanism 20 is in the locked position.

As the force F increases on the tether 50, the biasing member 35 is compressed and the first frame section 32, spikes 31, and members 36 move towards the second frame section 33 (i.e., from left to right in FIG. 9). Continued movement eventually causes the first frame member 32 to contact against the second frame section 33. Continued movement of the tether 50 causes just the spikes 31 and the members 36 to continuing moving towards the second frame section 33. This movement causes the extensions 37 on the members 36 to move inward from the contact ends 48 of the first frame section 32. This in turn causes the spikes to pivot with the contact edges 39 moving away from the tether 50. This allows the tether 50 to move through the release mechanism 20 and anchor 40 and reduce the tension. In one embodiment, the pivoting results in the spikes 31 being substantially parallel.

Once the tether 50 moves enough to reduce the tension below a predetermined amount, the biasing member 35 forces the first frame section 32, spikes 31, and members 36 along the tether 50 to reset the release mechanism 20 to the locked position. The process may then repeat if tension is again increased on the tether 50.

The various release mechanisms 20 may be attached to a shaft 41 for attachment within the patient. FIGS. 4, 5, and 6 illustrate examples of these embodiments. The release mechanisms 20 may also be positioned within the patient without shafts 41. These release mechanisms 20 are operatively connected to the tether 50 and positioned in the patient in other manners. FIG. 9 includes one embodiment with the release mechanism 20 abutting against an anchor 40.

One release mechanism includes a resorbable release mechanism that releases tension on a tether. This release mechanism is disclosed in U.S. patent application Ser. No. 11/676,649 filed on Feb. 20, 2007, and is herein incorporated by reference.

The various embodiments of the release mechanism 20 releases tension on the tether 50. In the embodiment of FIG. 4, the body 21 includes opposing first and second sections 23, 25 each with apertures 24, 26 that include contact edges. In use, the distance between the sections 23, 25 changes. In the locked position, the sections 23, 25 are positioned a first greater distance apart with the apertures 24, 26 positioned to prevent the tether 50 from moving through the body 21. In the release position, the sections 23, 25 are in closer proximity and the apertures 24, 26 are aligned to allow the tether 50 to move through the body 21.

In the embodiment of FIG. 6, the gates 28 form opposing first and second sections that each includes a contact edge 29 to contact the tether 50. The gates 28 are movable to adjust a relative angle of the gates 28 and a distance between the contact edges 29. In the locked position, the gates 28 form a first angle and the contact edges 29 are positioned a distance apart to engage the tether 50 and prevent movement. In the release position, the gates 28 are positioned at a different angle and the contact edges 29 are positioned a greater distance apart to allow movement of the tether 50.

In the embodiment of FIG. 9, the spikes 31 are positioned in an opposing orientation and each includes a contact edge 39. The angle formed by the opposing spikes 31 and the distance between the contact edges 39 may be changed. In the locked position, the spikes are positions at a first angle and the contact edges 39 a first distance apart. In the release position, the spikes 31 are positioned at a second angle and the contact edges 39 are positioned a greater distance apart to allow movement of the tether 50.

The tethering system 10 may be used to treat a wide variety of ailments. One type includes spinal deformities. The primary indications will be progressive idiopathic scoliosis with or without sagittal deformity in either infantile or juvenile patients. One patient population upon which to practice these embodiments is prepubescent children (before growth spurt) less than ten years old. Other patient groups upon which the embodiments may be practiced include adolescents from 10-12 years old with continued growth potential. It should be understood that fusionless tethering may also be used on older children whose growth spurt is late or who otherwise retain growth potential. It should be further understood that fusionless tethering may also find use in preventing or minimizing curve progression in individuals of various ages.

Generally, in the case of scoliosis, tethering will take place on the convex side of the curve. In one embodiment, the tether 50 is implanted with an anterior, minimally invasive (thoracoscopic) procedure on the convex side of the spinal curve. The tether 50 may be delivered into the patient in a minimally invasive approach using thoracoscopic instrumentation. The tether 50 may also be delivered in a posterior procedure, or some combination of both anterior and posterior. Finally, it should be understood that if the procedure fails to correct the curve but does, in fact, prevent further progression (which includes increase in the magnitude of the curve) it can and should be considered successful.

It should be understood that scoliosis is but one of many types of spinal deformities that can be addressed by the devices and techniques of the present application. Most commonly the devices and methods are expected to be used for either primary thoracic or thoracolumbar curves. They can be used for correction of the thoracic curve as an isolated curve, or the lumbar curve as an isolated curve.

The devices and methods may be used to treat spinal deformities in the coronal plane, such as a scoliotic spine illustrated in FIG. 2. The devices and methods may also be used to treat deformities in the sagittal plane, such as a kyphotic spine or Scheurmann's kyphosis.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The contact edges in the various embodiments may be smooth, or may include teeth or other gripping structures to facilitate engagement with the tether 50. The present embodiments are, therefore, to be considered in all respects as illustrative and not restrictive, and all changes coming within the meaning and equivalency range of the appended claims are intended to be embraced therein.

What is claimed is:

1. A release mechanism to release tension on a surgical tether comprising:
a body adapted to receive the tether including a first section defining a first axis and comprising an aperture extending substantially perpendicular to the first axis, the body including a second section defining a second axis and comprising an aperture extending substantially perpendicular to the second axis, the first and second sections being connected to one another by a bend portion continuous with the first and second sections, the apertures being configured for disposal of the tether, each aperture including a contact edge configured to engage the tether, the bend portion comprising a flexible material such that the bend portion flexes to adjust a distance between the contact edges and a relative angle between the first and second sections in response to force applied to the tether;
the body configured to move in response to force applied to the tether, the body moves between a locked position and a release position, the locked position includes the first section positioned at a first angle relative to the second section and the contact edges positioned a first distance apart to engage the tether and prevent the tether from moving through the body, the release position includes the second section positioned at a different second angle relative to the second section and the contact edges being positioned a second distance apart to allow the tether to move through the body; the body being biased towards the locked position.

2. The release mechanism of claim 1, further comprising a shaft that extends outward from the body to attach the release mechanism within a patient.

3. The release mechanism of claim 1, wherein the tension is released when the amount of tension exceeds a predetermined amount.

4. The release mechanism of claim 1, wherein each of the first and second sections are straight.

5. The release mechanism of claim 1, wherein the body is configured with one of the first and second sections being stationary with the other of the first and second sections being movable to adjust the distance between the contact edges and the relative angle between the first and second sections.

6. A release mechanism to release tension on a surgical tether comprising:
a monolithic elongated body that includes an intermediate bend comprising a flexible material, the body including a first section on a first side of the bend defining a first axis and a second section on a second side of the bend defining a second axis;
a first aperture extending perpendicular to the first axis through the first section, the first aperture sized to receive the tether and includes a contact edge configured to engage the tether;
a second aperture extending perpendicular to the second axis through the second section, the second aperture sized to receive the tether and includes a contact edge configured to engage the tether;
the body being movable in response to a force applied to the tether, the tether applies a force to each contact edge causing the intermediate bend to flex such that the body moves between a locked position with the first section positioned at a first angle relative to the second section, and a release position with the first section positioned at a second, smaller angle relative to the second section;
the tether being fixedly positioned within the apertures when the body is in the locked position and movable within the apertures when the body is in the release position.

7. The release mechanism of claim 6, wherein the elongated body is constructed from a unitary, one-piece construction, the first axis is disposed at a first angle relative to the second axis when the body is in the locked position and the first axis is disposed at a second angle relative to the second axis when the body is in the release position, the second angle being less than the first angle.

8. The release mechanism of claim 6, wherein the elongated body is fixedly attached to a shaft to attach the release mechanism to a patient.

9. The release mechanism of claim 6, wherein one of the first and second sections is stationary while the body moves between the locked and release positions.

10. A release mechanism to release tension on a surgical tether comprising:
a unitary, one-piece body adapted to receive the tether including a first section defining a first axis and comprising an aperture extending substantially perpendicular to the first axis through the first section, the body including a second section defining a second axis and comprising a second aperture extending substantially perpendicular to the second axis through the second section, the first and second sections each including a contact edge configured to engage the tether, the first and second sections being connected to one another by a bend portion, the bend portion comprising a flexible material to allow the body to adjust a distance between the contact edges, in response to a force applied to the tether;
the body being movable in response to a force applied to the tether, the body moves between a locked position with the contact edges positioned to engage the tether and prevent the tether from moving through the body, and a release position with the contact edges positioned to allow the tether to move through the body;

the body being biased to remain in the locked position as tension on the tether increases and remains less than a predetermined amount, and to move to the release position once the tension reaches the predetermined amount.

11. The release mechanism of claim 10, wherein the body includes a shaft configured to attach the release mechanism to a patient, the shaft being parallel with the second axis when the body is in the locked position and disposed at an acute angle relative to the second axis when the body is in the release position.

* * * * *